(12) United States Patent
Quintana (10) Patent No.: US 10,959,799 B2
(45) Date of Patent: Mar. 30, 2021

(54) SYSTEMS, PRODUCTS AND METHODS FOR REDUCING GLOVE WASTE AND CONTAMINATION

(71) Applicant: Ellen Quintana, Cromwell, CT (US)

(72) Inventor: Ellen Quintana, Cromwell, CT (US)

( * ) Notice: Subject to any disclaimer, the term of this patent is extended or adjusted under 35 U.S.C. 154(b) by 0 days.

(21) Appl. No.: 16/380,893

(22) Filed: Apr. 10, 2019

(65) Prior Publication Data

US 2020/0323604 A1 Oct. 15, 2020

(51) Int. Cl.
*A61B 42/40* (2016.01)
*B65D 83/08* (2006.01)

(52) U.S. Cl.
CPC .......... *A61B 42/40* (2016.02); *B65D 83/0805* (2013.01)

(58) Field of Classification Search
USPC ..................................................... 221/33–63
See application file for complete search history.

(56) References Cited

U.S. PATENT DOCUMENTS

| | | | |
|---|---|---|---|
| 6,062,421 A | 5/2000 | Marley | |
| 6,585,131 B2 | 7/2003 | Huang et al. | |
| 7,134,572 B2 | 11/2006 | Morin | |
| 7,600,641 B2 * | 10/2009 | Burgess | B65D 75/5838 206/233 |
| 7,842,365 B2 * | 11/2010 | Riggs | G09F 3/0292 220/359.1 |
| 2002/0179627 A1 * | 12/2002 | Huang | B65D 83/0805 221/63 |
| 2005/0048124 A1 | 3/2005 | Sarangapani | |
| 2008/0314920 A1 | 12/2008 | Rodrigues | |
| 2012/0160864 A1 | 6/2012 | Shoaf et al. | |
| 2012/0160865 A1 * | 6/2012 | Lien | A61B 42/40 221/45 |
| 2014/0061220 A1 * | 3/2014 | Kowal | B65D 85/18 221/135 |
| 2017/0349353 A1 | 12/2017 | Yao et al. | |

OTHER PUBLICATIONS

Kimberly-Clark, New SmartPULL dispensing system, adversisement. Printed Mar. 5, 2019. (1 page).

* cited by examiner

*Primary Examiner* — Gene O Crawford
*Assistant Examiner* — Ayodeji T Ojofeitimi
(74) *Attorney, Agent, or Firm* — UConn IP Law Clinic; Gabrielle Gelozin; Joseph Conte (57) ABSTRACT

A device for reducing glove waste comprising a flexible sheet configured to be adhered to a glove dispensing box, the flexible sheet having a non-linear, elongated slit dimensioned to permit passage of a glove therethrough, and an antimicrobial additive disposed to inhibit bacterial growth proximate the slit. Also disclosed herein are accompanying methods and systems for reducing glove waste and contamination.

20 Claims, 7 Drawing Sheets

Fig. 12

SYSTEMS, PRODUCTS AND METHODS FOR REDUCING GLOVE WASTE AND CONTAMINATION

BACKGROUND

1. Field

The disclosed embodiments relate to single use glove waste reduction and more particularly, systems and methods for reducing waste of single use gloves and reducing contamination in sterile environments.

2. Description of Related Art

Systems and methods meant to reduce single use glove waste are currently known in the art. Single use gloves often come in a standard rectangular box with a single rectangular or elliptical opening to allow for removal of a plurality of gloves. In doing so, it is common that more than one glove is removed from the box, causing it to fall into a contaminated area and thus it can no longer be used. This removal of excess gloves causes a considerable amount of waste and can significantly increase the operating costs of a facility. Additionally, such a large opening in the top of the box allows for easier contamination of the gloves that remain in the box.

Current systems and methods meant to control glove waste and contamination include arc shaped films covering the existing opening, containers with a restricted opening where the box of gloves is placed in the container, methods for folding the gloves for more efficient removal, and boxes with smaller openings. Such conventional techniques have generally been considered satisfactory for their intended purpose. However, when using traditional methods, single pull failure rates are still relatively high, and traditional methods have not included a method for reducing glove waste and reducing contamination within the same method or system. There remains a need in the art for a system and method that will both reduce glove waste and reduce contamination. There is also a need for a system and method that is disposable and efficient to implement.

SUMMARY

The disclosed embodiments relate to a new and useful way to reduce glove waste and contamination. One embodiment disclosed herein is a device for reducing glove waste comprising a flexible sheet configured to be adhered to a glove dispensing box, where the flexible sheet has a non-linear, elongated slit dimensioned to permit passage of a glove therethrough, and the flexible sheet contains an antimicrobial additive disposed to inhibit bacterial growth proximate the slit. In embodiments, the device comprises an elastic polymer. The polymer can be an elastic thermoset material and/or an elastic thermoplastic material. In some cases, the device is made of a synthetic rubber or a variety of other materials suitable for the purpose. The nonlinear slit of the device can have a generally sinusoidal pattern. In embodiments, the flexible sheet has a generally uniform thickness, and in some cases the slit has a length that is longer than the length of an existing opening on the glove dispensing box. The device also can have an adhesive that is pre-applied to the flexible sheet and is covered by a protective sheet before use. The device further has an antimicrobial additive that can be incorporated into the flexible sheet during manufacture, or the antimicrobial additive is applied to a surface of the flexible sheet after manufacture. The device can be the flexible sheet and adhesive contained in a package.

Another embodiment herein relates to a method for reducing glove waste comprising forming a flexible sheet, forming an elongated, narrow opening in the flexible sheet, applying an adhesive layer to a portion of one side of the flexible sheet and disposing a protective covering over the adhesive layer, removing the protective covering from the flexible sheet, and attaching the flexible sheet over an opening in a glove dispensing box using the adhesive layer.

The disclosed embodiments also relate to a system for reducing glove waste, comprising a glove dispensing box having a first opening through which gloves can be manually pulled, a flexible sheet positioned over the first opening in the glove dispensing box, the sheet having a non-linear, elongated slit dimensioned to provide for passage of an individual glove and to inhibit the passage of multiple gloves with a single manual pull, and an antimicrobial additive disposed to inhibit bacterial growth proximate the slit. The system can be the flexible sheet and adhesive contained in a package and later removed from the package when ready to be applied to a glove dispensing box.

BRIEF DESCRIPTION OF THE DRAWINGS

The disclosed embodiments, both as to organization and method of practice, together with the further objects and advantages thereof, may best be understood by reference to the following description taken in connection with the accompanying drawings in which:

FIG. 3 is a front view of the first embodiment of the flexible sheet attached to a box of gloves, a back view being similar.

FIG. 4 is an exploded view showing how the first embodiment of the flexible sheet is attached to the box of gloves.

DETAILED DESCRIPTION OF THE PREFERRED EMBODIMENTS

One embodiment disclosed herein is a glove waste reduction system that also functions as an antimicrobial barrier, thus simultaneously preventing excess glove waste and reducing the chances of contamination. Conventional methods for reducing glove waste typically include folding the gloves in a particular manner during packaging, enclosing the box of gloves in a housing, or reducing the size of the orifice where the gloves are removed. However, the difficulty with each of these methods is that none function both as a barrier to contaminants and also as a device that reduces excess glove waste. With the disclosed embodiments, a user places a flexible, sheet-like layer with an incorporated antimicrobial additive over top of the already opened box of gloves. The width of the slit in the flexible sheet is smaller than the width of the existing opening in the box of gloves, and is characterized by a generally sinusoidal shape that extends laterally across the flexible sheet. The sheet has a frictional strength that is able to overcome the frictional attraction of the gloves to one another. This allows the user to pull only one glove at a time, while any attached gloves are stripped away and remain in the box with no part exposed. The antimicrobial additive is able to prevent excessive growth of harmful bacteria, and is effective in killing unhealthy germs. In some cases, the antimicrobial additive includes a silver-containing material such as silver nitrate. Non-limiting examples of other silver-containing antimicrobial compounds include silver glass, colloidal silver, and silver nanoparticles. The antimicrobial additive prevents the gloves remaining in the box from becoming contaminated with outside pollutants, or any contaminants that were on the user's hands when the glove was retrieved. While an additive containing silver nitrate is preferred, one skilled in the art would readily appreciate that the make-up of the antimicrobial additive can be determined based on the specific need for the environment and/or the material used for the flexible sheet without deviating from the scope of this disclosure. An additional advantage of the disclosed embodiments over conventional methods is that the flexible sheet is disposable and can be thrown away with an empty box of gloves. This eliminates the time needed to wash a box housing between uses on various boxes of gloves. The system as described in this application presents a much more efficient way of reducing glove waste and reducing contamination than previously known methods.

Reference will now be made to the drawings wherein like reference numerals identify similar structural features or aspects of the subject invention. For purposes of explanation and illustration, and not limitation, a partial view of an exemplary embodiment of the glove waste reduction device comprising a flexible sheet in accordance with the invention is shown in FIG. 1 and is designated generally by reference character 100.

Figures 1, 2:
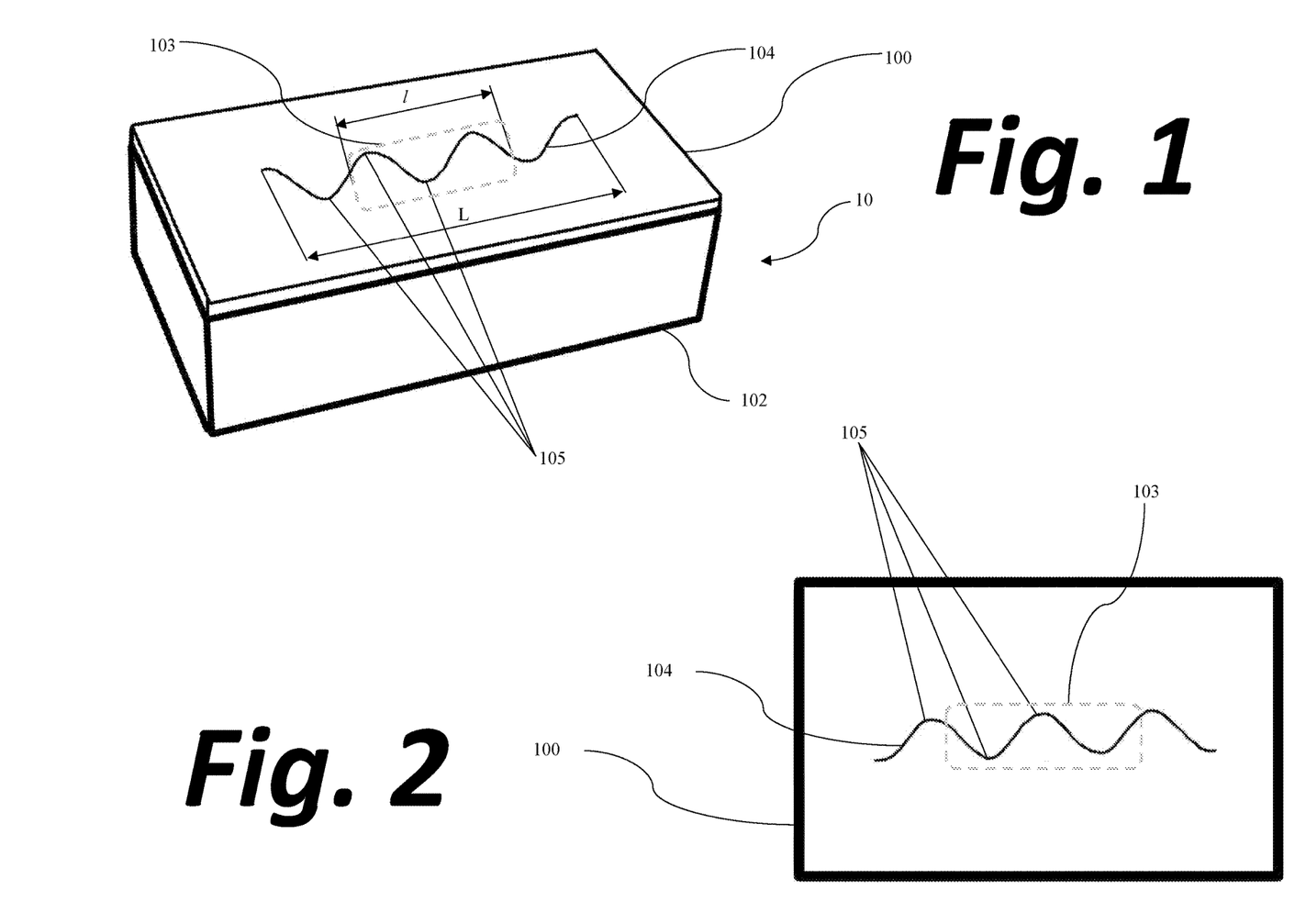
FIG. 1 is a perspective view of a first embodiment of a flexible sheet attached to boxes of gloves.
FIG. 2 is a top view of the first embodiment of the flexible sheet.

With reference now to FIGS. 1 and 2, sheet 100 is configured to be attached to box of gloves 102 using an adhesive that can be either present on sheet 100, present on box of gloves 102, or separately applied to one of the sheet and the box. The sheet 100 and box 102 together form a system 10. In embodiments, the adhesive is applied to the sheet before packaging of the sheet, and a peelable backing layer similar to the backing layer on an adhesive bandage covers the adhesive layer.

Figure 7:
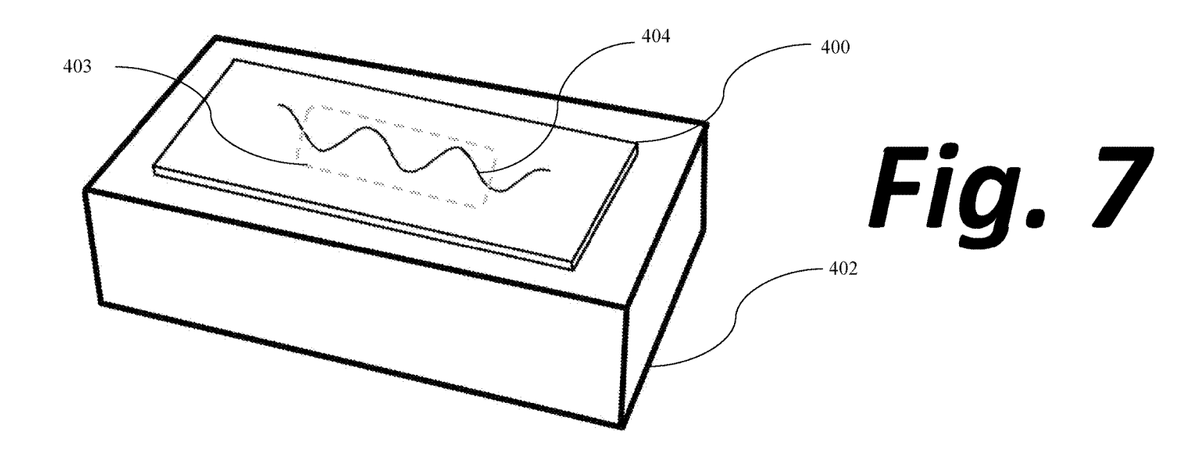
FIG. 7 is a left perspective view of a flexible sheet which is smaller than the size of the box of gloves.
Figure 8:
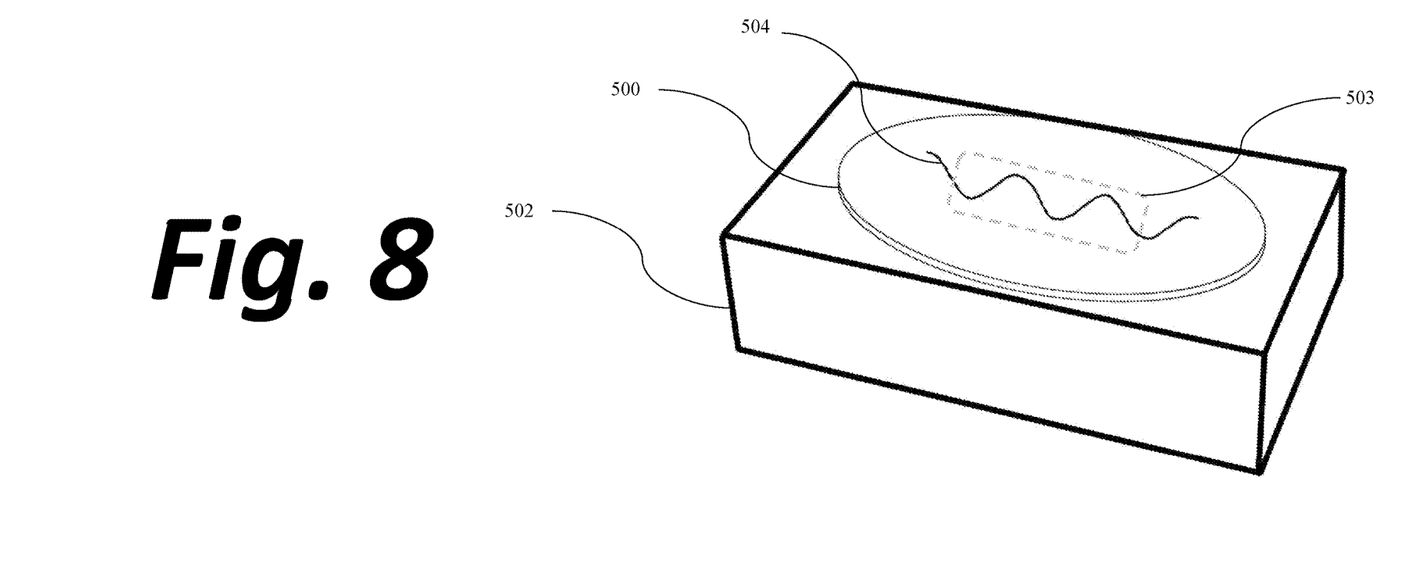
FIG. 8 is a left perspective view of a flexible sheet which has a non-rectangular shape and is smaller than the size of the box of gloves.
Figure 9:
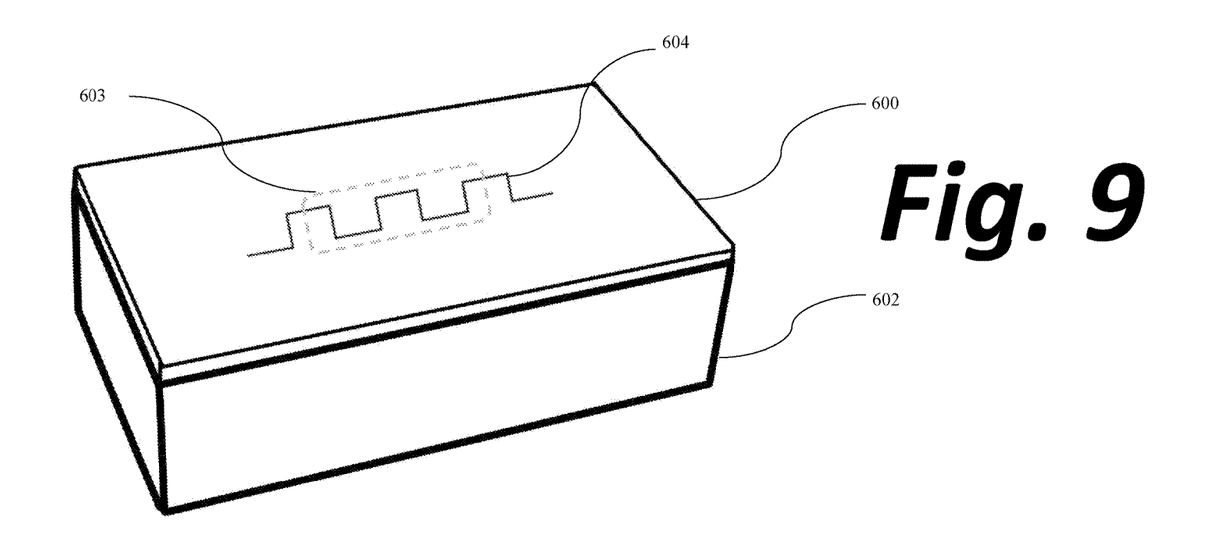
FIGS. 9-10 are a perspective views of flexible sheets having non-linear, non-sinusoidal slits.
Figure 10:
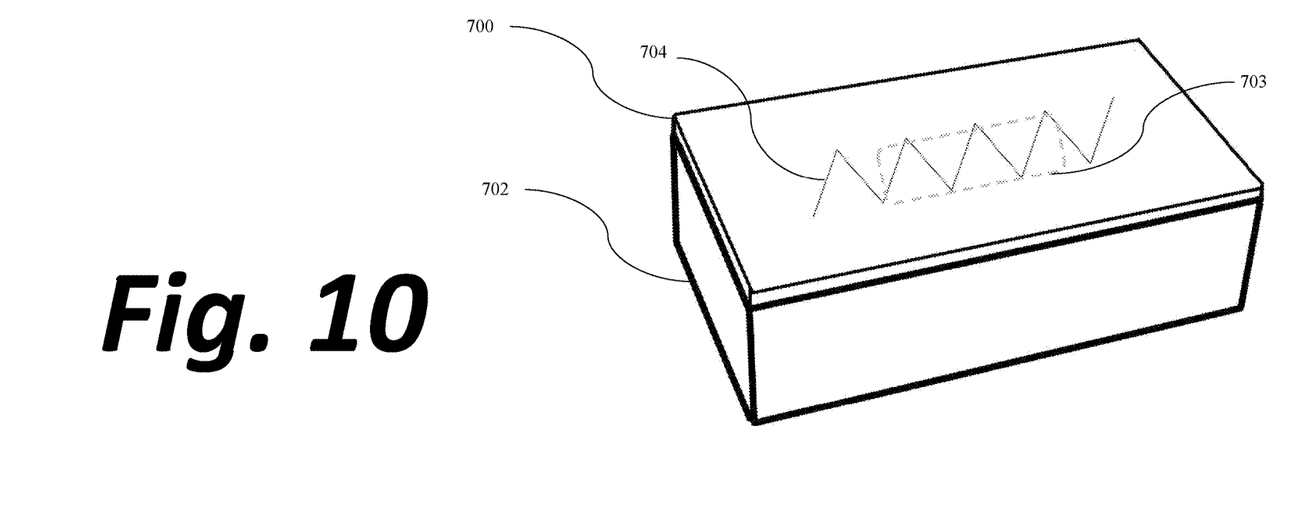

The sheet has an elongated slit 104 formed therein. While shown in the FIGS. 1 and 2 to be generally sinusoidal, slit 104 can be a non-liner slit of shapes as shown in FIGS. 9 and 10. Slits having other suitable shapes also can be used. Slit 104 can be substantially aligned with, and in direct contact with the existing opening 103, for example, slit 104 is aligned over top of the existing opening 103 in box of gloves 102 so that gloves may be retrieved one at a time. Slit 104 prevents any part of the next glove from being exposed and slit 104 is meant to close after extraction of a glove so that contaminants may not enter box of gloves 102. There is a negligible amount of negative space between the opposing sides of slit 104, as slit 104 is generally formed by slicing. Slit 104 can also have a distance (in the direction of width) of about 0.5 mm 2 mm if formed by removing material in the shape of slit 104. In embodiments, slit 104 has a number of peaks 105 equal in the range of three to eight, or three to six, for maximum efficacy. Sheet 100 can have a length and/or a width approximately equal to the size of box of gloves 102 as shown in FIG. 1, but can also be of any smaller shape so long as slit 104 is able to cover the existing opening 103 of box of gloves 102, as seen in FIGS. 7 and 8. In FIG. 1, existing opening 103 has a length of l, and slit 104 has a length of L. In embodiments, slit 104 has a length of L which can be about between about 7 cm to about 25 cm, or about 13 cm to about 20 cm, or about 15 cm to about 17 cm. Commercial glove boxes typically have an opening of length l ranging from about 9 cm to about 13 cm. In some cases, slit 104 is dimensioned to be have a length L that is greater than the length l of the existing opening. In the embodiment shown in FIG. 1, the antimicrobial additive is incorporated into the sheet 100 during the manufacture of the sheet material from which the sheet 100 is cut.

Figures 3, 4:
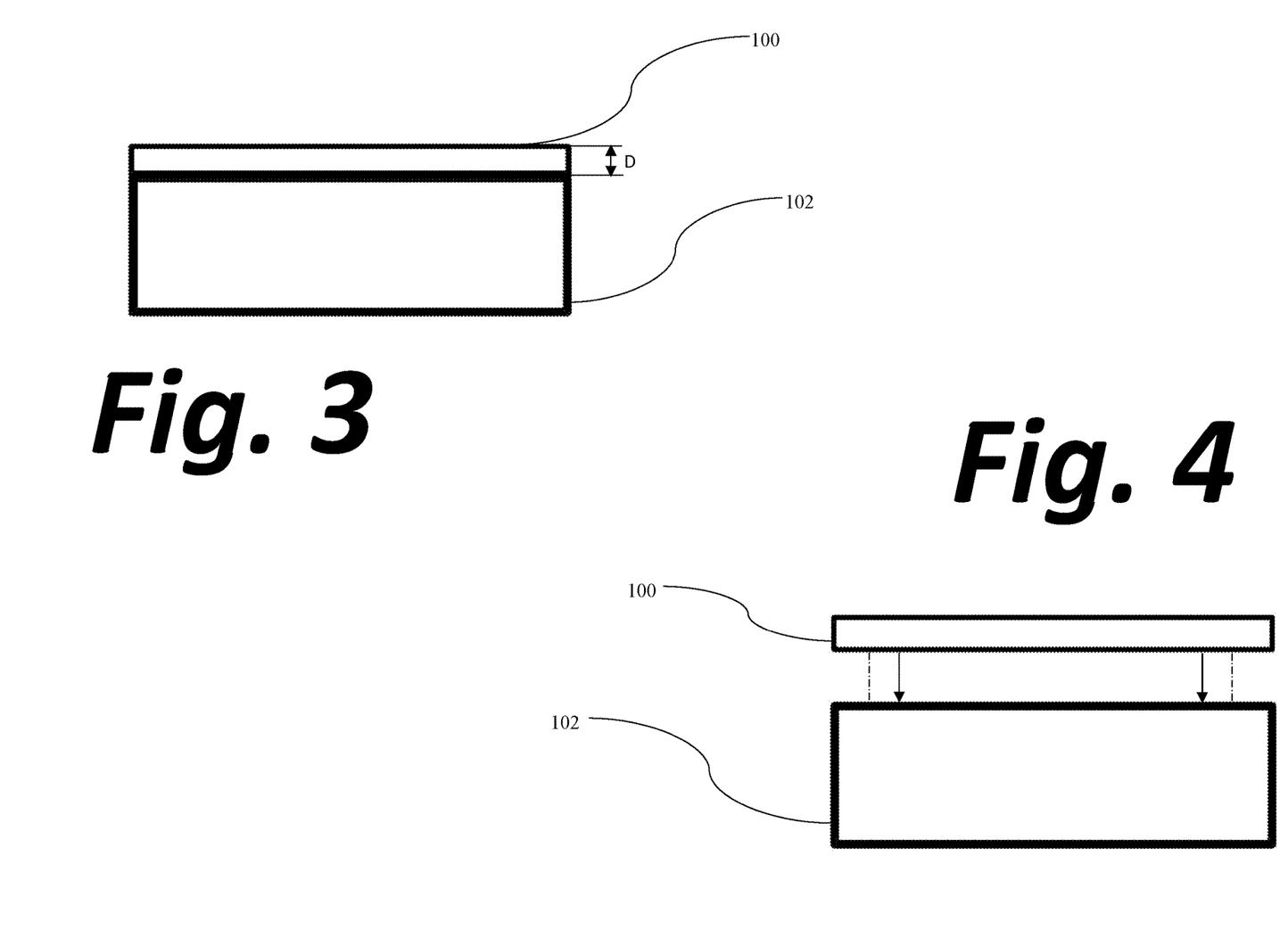
Figures 5, 6:
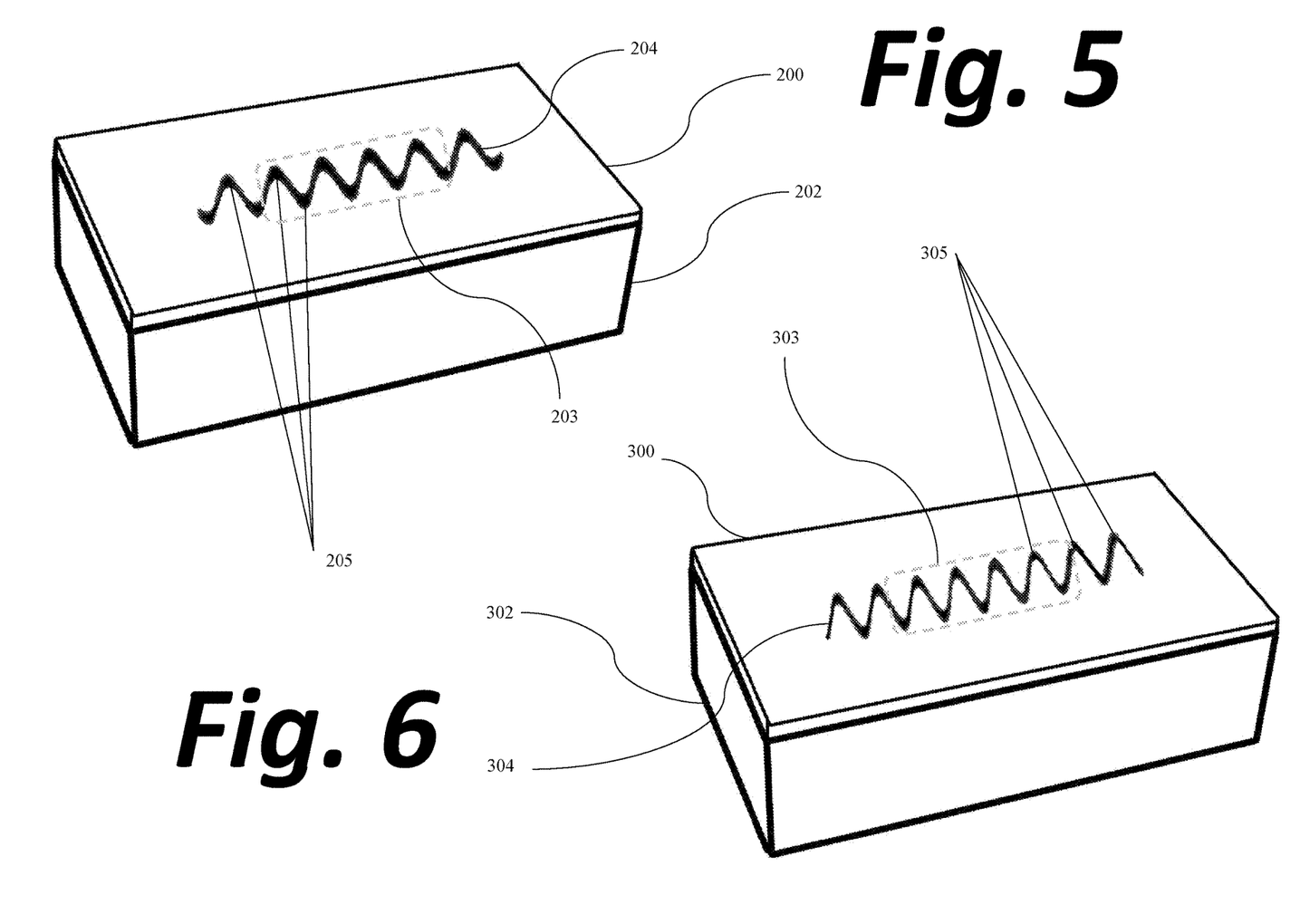
FIGS. 5-6 are a perspective views of embodiments where the flexible sheet has a non-linear, sinusoidal slit with more peaks than the first embodiment.

With reference now to FIG. 3, sheet 100 has a thickness of D. One skilled in the art would readily appreciate that the thickness of the flexible sheet can vary and should be chosen based on the rigidity and strength of the material of the flexible sheet. In embodiments, D is in the range of about 1 mm to about 10 mm, or about 1.5 mm to about 6 mm, or about 2 mm to about 4 mm, and is attached to box of gloves 102 using an adhesive backing. As seen, there is no space between box of gloves 102 and sheet 100 when sheet 100 is attached to box of gloves 102. Sheet 100 is directly adhered to an outer surface of a box of gloves 102. The gloves 102 are in direct contact with the inner wall of the box of gloves 102.

Figure 11:
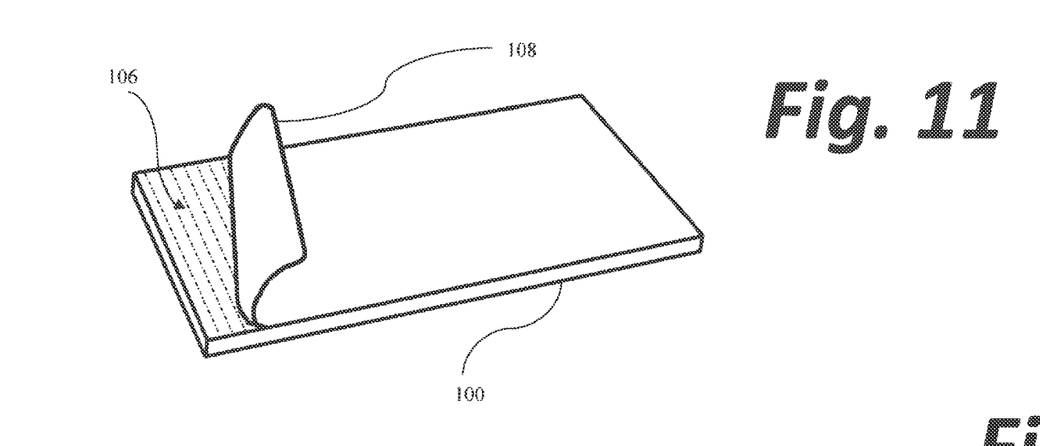
FIG. 11 is a perspective bottom view of the first embodiment showing how the adhesive backing is exposed for attaching to a box of gloves.
Figure 12:
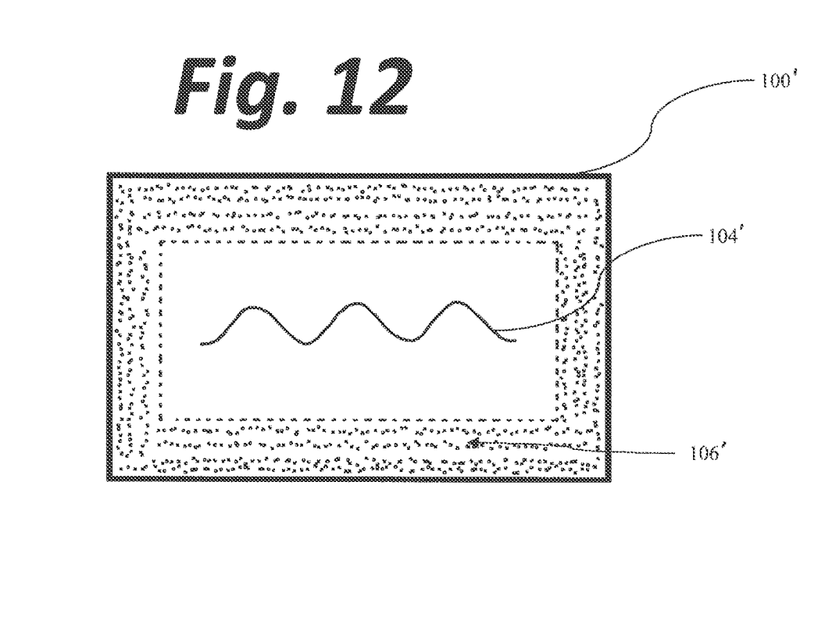
FIG. 12 is a bottom view of a flexible sheet showing a peripheral adhesive coating.
Figure 13:
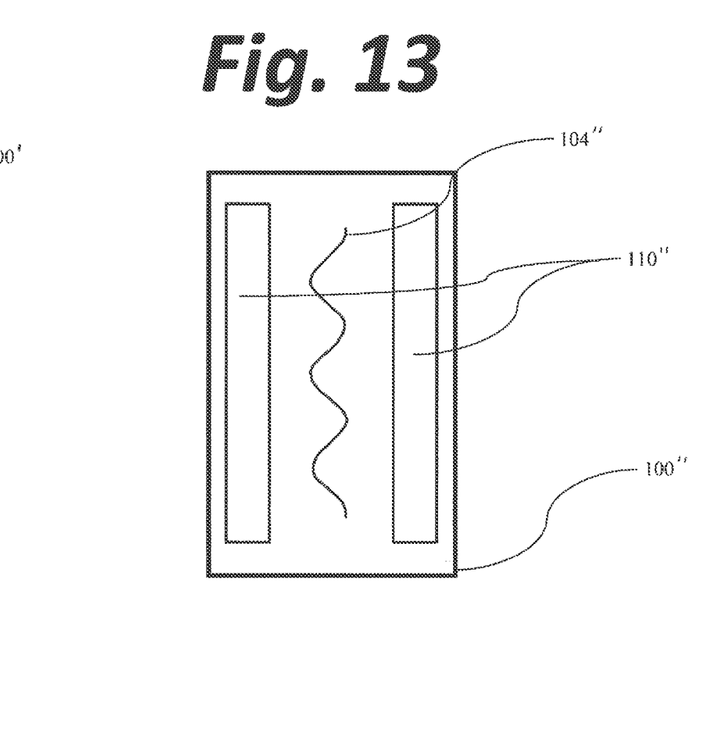
FIG. 13 is a bottom view of flexible sheet showing a method of adhering the flexible sheet to the box of gloves using two sided adhesive tape.
Figures 14, 15:
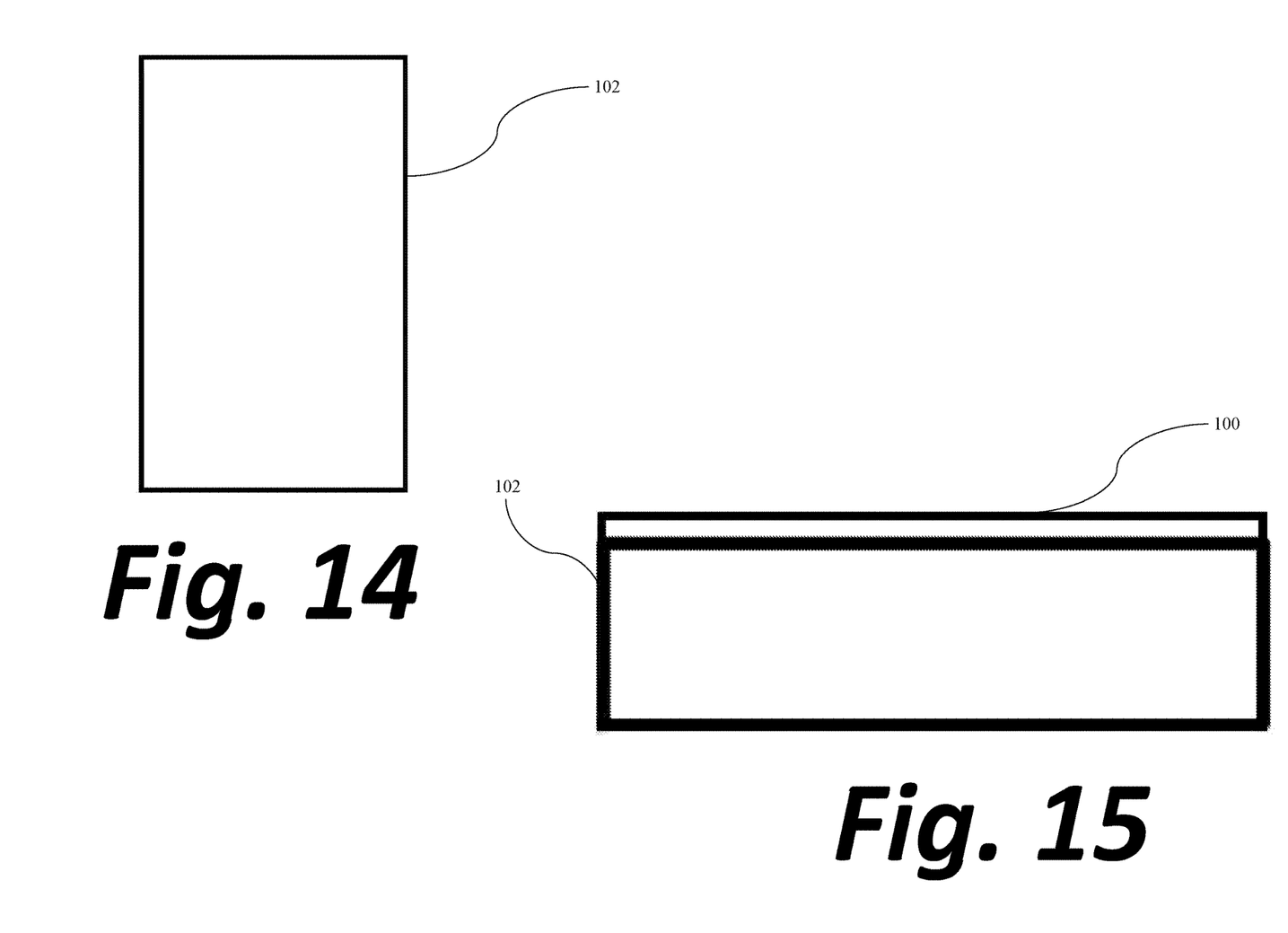
FIG. 14 is a bottom view of a box of gloves having a flexible sheet attached thereto.
FIG. 15 is a left side view of the flexible sheet attached to the box of gloves, a right side view being identical thereof.

Referring now to FIG. 4, this drawing shows an exploded view of one way in which sheet 100 may be attached to box of gloves 102. An adhesive backing, shown as 106 and 110 in FIGS. 11-13, is exposed by removing protective sheet 108 as shown in FIG. 11. Once protective sheet 108 is removed, adhesive backing 106 can be placed onto box of gloves 102 so that sheet 100 is adhered to box of gloves 102. Adhesive backing 106" can be a number of pieces of double sided tape 110", as shown on sheet 100" in FIG. 13, or adhesive backing 106' can applied to any portion of sheet 100' that does not cover slit 104', for example along the periphery of sheet 100' as shown in FIG. 12.

Referring now to FIGS. 7 and 8, sheet 100 can be generally the size of box of gloves 102 as shown in FIGS. 1-5. However, sheet 500 can also be of any size that allows for slit 504 to meet the length necessary to effectively cover existing opening 503, as shown in FIG. 8. Sheet 500 has an elliptical shape. In FIG. 7, sheet 400 has a rectangular shape that is smaller in both length and width than the box of gloves 402. Slit 404 extends along most of the length of sheet 400.

Sheet 600 is also not limited to a generally rectangular shape but can be have any shape that allows for slit 604 to meet the length necessary to effectively cover existing opening 603, as shown in FIG. 9.

Sheet 100 is generally not larger than box of gloves 102. In embodiments, sheet 100 is of a material that is soft enough to be cut by the user should sheet 100 initially extend beyond the dimensions of box of gloves 102. Sheet 100 is flexible to allow peaks 105 to bend during removal of a glove, but rigid enough so that peaks 105 provide enough friction to prevent multiple gloves from being pulled during extraction. The flexible nature of sheet 100 allows for peaks 105 to return to their starting position, thereby reducing the ability of contaminants to enter box of gloves 102. Sheet 100 has a coefficient of friction f, where f is in the range of about 0.1 to about 3, or about 1 to about 3, or about 1.5 to about 1.9, when interacting with nitrile gloves. It is expected that sheet 100 has a coefficient of friction f in the range of about 0.1 to about 3, or about 1 to about 3, or about 1.5 to about 2, when interacting with gloves formed from neoprene, vinyl, latex, or another elastic glove material.

Slit 104 has a width that is smaller than the width of an existing opening 103 in box of gloves 102. In some cases, the length of slit 104 is smaller than the length of the existing opening 103 in box of gloves 102. The width of space between the two sides of slit 104 typically is within the range of about 0 mm to about 1 mm. Slit 104 can be formed by simply cutting the sheet, resulting in an opening having a width of about 0 mm, or by removing a thin section of material. In embodiments, slit 104 is has a width perpendicular to length L that is smaller than the width perpendicular to length l of existing opening 103.

Sheet 100 is generally made using a synthetic rubber material, however sheet 100 can also be created from a variety of thermoplastic elastomers and thermoset elastomers, including but not limited to neoprene, polychloroprene, polyisoprene, nitrile butadiene rubber, silicone rubber, nitrile rubber, ethylene propylene diene terpolymer (EPDM rubber), or the like. Each of the alternative materials has generally similar flexibility properties, similar tensile strengths, similar ability to be sterilized and incorporate antimicrobial additives, and can be substituted depending on need. The material of sheet 100 may be chosen based on the desired properties but will generally have a durometer hardness of about 20 A to about 80 A, or about 30 A to about 70 A, or about 40 A to about 60 A, where durometer hardness is measured using the Shore A scale. Sheet 100 is to have an antimicrobial component. The antimicrobial component can be incorporated into sheet 100 during manufacture, or the antimicrobial component can be added to sheet 100 as a spray coating, dip coating, roll-on-coating, brush coating, etc. when manufacture is complete. The antimicrobial coating can be applied before or after the slit 104 is formed in the sheet 100. The antimicrobial coating can be applied to the entire sheet 100 or only to the portions of the sheet 100 proximate the slit. In some cases, the antimicrobial coating is applied in a layer that extends about 1-2 cm around the slit. In some cases, the antibacterial coating is applied only to the outer surface of the sheet, while in other cases the antibacterial coating is applied to both the outer surface and the underlying surface of the sheet.

While the invention has been described in detail herein in accordance with certain preferred embodiments thereof, many modifications and changes therein may be effected by those skilled in the art. Accordingly, it is intended by the appended claims to cover all such modifications and changes as fall within the spirit and scope of the invention.

What is claimed:

1. A system for reducing glove waste, comprising:
   a glove dispensing box comprising a set of gloves and having a first opening through which gloves can be manually pulled;
   a flexible sheet positioned adjacent to and in direct contact with the first opening in the glove dispensing box, the sheet having a nonlinear, elongated sinusoidal slit dimensioned to provide for passage of an individual glove and to inhibit passage of multiple gloves with a single manual pull; and
   an antimicrobial additive disposed to inhibit bacterial growth proximate the slit,
   wherein the flexible sheet and an adhesive are contained in a package and removed from the package when ready to be applied to the glove dispensing box.

2. The system as recited in claim 1, wherein the flexible sheet has a generally uniform thickness that is in the range of about 1 mm to about 5 mm, and wherein the slit has a length that is longer than a length of the first opening in the glove dispensing box.

3. The system as recited in claim 1, wherein the antimicrobial additive is incorporated into the flexible sheet during manufacture.

4. A device for reducing glove waste, comprising:
   a flexible sheet configured to be adhered to a glove dispensing box, the flexible sheet having a nonlinear, elongated slit dimensioned to permit passage of a glove therethrough; and
   an antimicrobial additive disposed to inhibit bacterial growth proximate the slit,
   wherein an adhesive is pre-applied to the flexible sheet and is covered by a protective sheet before use, and
   wherein the flexible sheet and the adhesive are contained in a package.

5. The device as recited in claim 4, wherein the flexible sheet comprises synthetic rubber.

6. The device as recited in claim 4, wherein the slit has a sinusoidal configuration.

7. The device as recited in claim 4, wherein the flexible sheet has a generally uniform thickness that is in the range of about 1 mm to about 5 mm, and wherein the slit has a length that is longer than a length of an existing opening on the glove dispensing box.

8. The device as recited in claim 4, wherein the antimicrobial additive is incorporated into the flexible sheet during manufacture.

9. The device as recited in claim 4, wherein the antimicrobial additive is applied to a surface of the flexible sheet after manufacture.

10. A method for reducing glove waste, comprising:
    forming a flexible sheet;
    forming an elongated, narrow slit in the flexible sheet, wherein the slit is narrow along its entire length;
    applying an adhesive layer to a portion of one side of the flexible sheet and disposing a protective covering over the adhesive layer;
    removing the protective covering from the flexible sheet; and
    attaching the flexible sheet adjacent to and in direct contact with an opening in a glove dispensing box using the adhesive layer.

11. The method as recited in claim 10, wherein the flexible sheet comprises synthetic rubber.

12. The method as recited in claim 10, wherein the flexible sheet has a generally uniform thickness in the range of about 1 mm to about 5 mm, and wherein the length of the slit is longer than a length of the opening in the glove dispensing box.

13. The method as recited in claim 10, wherein the slit has a width in a range of 0 to 1 millimeter.

14. The method as recited in claim 10, further comprising incorporating an antimicrobial material into the flexible sheet proximate the elongated, narrow slit.

15. The method as recited in claim 14, wherein the antimicrobial material is incorporated into the flexible sheet during manufacture of the sheet.

16. A system for reducing glove waste, comprising:
- a glove dispensing box comprising a set of gloves and having a first opening through which gloves can be manually pulled;
- a flexible sheet positioned adjacent to and in direct contact with the first opening in the glove dispensing box, the sheet having a nonlinear, elongated sinusoidal slit dimensioned to provide for passage of an individual glove and to inhibit passage of multiple gloves with a single manual pull; and
- an antimicrobial additive disposed to inhibit bacterial growth proximate the slit,
- wherein an adhesive layer is pre-applied to the flexible sheet and is covered by a protective covering until the flexible sheet is to be positioned over the first opening.

17. The system as recited in claim 16, wherein the flexible sheet comprises synthetic rubber.

18. The system as recited in claim 16, wherein the flexible sheet has a generally uniform thickness that is in the range of about 1 mm to about 5 mm, and wherein the slit has a length that is longer than a length of the first opening on the glove dispensing box.

19. The system as recited in claim 16, wherein the antimicrobial additive is incorporated into the flexible sheet during manufacture.

20. The system as recited in claim 16, wherein the flexible sheet and a-R the adhesive layer are contained in a package and removed from the package when ready to be applied to a glove dispensing box.

\* \* \* \* \*